US00PP26692P3

(12) United States Plant Patent
Sato et al.

(10) Patent No.: US PP26,692 P3
(45) Date of Patent: May 3, 2016

(54) **NEW GUINEA *IMPATIENS* PLANT NAMED 'SAKIMP029'**

(50) Latin Name: *Impatiens hybrida hort*
Varietal Denomination: SAKIMP029

(71) Applicant: Sakata Seed Corporation, Yokohama (JP)

(72) Inventors: Chihiro Sato, Nagano (JP); Shinji Minemura, Nagano (JP)

(73) Assignee: Sakata Seed Corporation, Yokohama (JP)

( * ) Notice: Subject to any disclaimer, the term of this patent is extended or adjusted under 35 U.S.C. 154(b) by 175 days.

(21) Appl. No.: 13/998,935

(22) Filed: Dec. 23, 2013

(65) Prior Publication Data

US 2015/0181794 P1 Jun. 25, 2015

(51) Int. Cl.
*A01H 5/02* (2006.01)

(52) U.S. Cl.
USPC ..... Plt./318.6

(58) Field of Classification Search
USPC ..... Plt./318.6
See application file for complete search history.

*Primary Examiner* — Keith Robinson
(74) *Attorney, Agent, or Firm* — Barbara Campbell; Bethany R. Roahrig; Cochran Freund & Young, LLC

(57) ABSTRACT

A New Guinea *Impatiens* plant particularly distinguished by having a magenta flower color, strong root system and a vigorous growth habit, is disclosed.

2 Drawing Sheets

Genus and species: *Impatiens hybrida hort.*
Variety denomination: 'SAKIMP029'.

BACKGROUND OF THE NEW PLANT

The present invention comprises of a new and distinct cultivar of New Guinea *Impatiens*, botanically known as *Impatiens hybrida hort*, and referred to by the variety name 'SAKIMP029'. Line 'SAKIMP029' originated from a controlled cross between the female *Impatiens* line 'NE-5331', an unpatented proprietary *Impatiens* breeding line with a salmon flower color and the male *Impatiens* line 'NH-312', an unpatented proprietary *Impatiens* breeding line with a red flower color in Misato, Japan.

In June 2008, the female parent line 'NE-5331' and male parent line 'NH-312' were crossed and a population of $F_1$ plants was created having magenta flower color, strong root system and a vigorous habit . The $F_1$ plants were evaluated in Misato, Japan in an open field trial. The criteria for plant selection included a red flower color, strong root system and a vigorous habit. At the completion of the trial, one single-plant selection was made and vegetatively propagated. From May 2010 to August 2010, the selection was evaluated in an open field in Misato, Japan. The selection subsequently was named 'SAKIMP029' and found to have its unique characteristics reproduce true to type in successive generations of asexual vegetative propagation in Salinas, Calif.

SUMMARY

The following are the most outstanding and distinguishing characteristics of this new variety when grown under normal horticultural practices in Salinas, Calif.

1. Magenta flower color;
2. Strong root system; and
3. Vigorous habit.

DESCRIPTION OF THE PHOTOGRAPHS

This *Impatiens* plant is illustrated by the accompanying photographs which show the plant's overall plant habit including form, foliage, and flowers. The photographs are of a four-month-old plant grown in Salinas, Calif. under greenhouse conditions in the spring of 2013. The colors shown are as true as can be reasonably obtained by conventional photographic procedures.

DESCRIPTION OF THE NEW VARIETY

Figure 1:
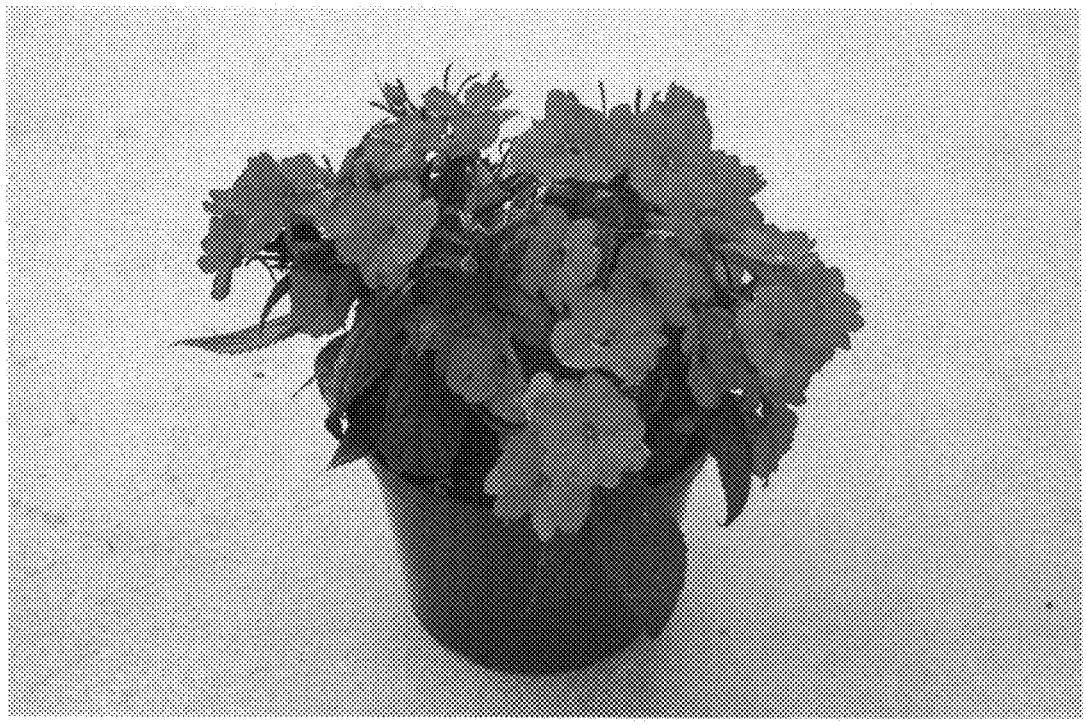
FIG. 1 shows the overall plant habit of the plant grown in a pot.
Figure 2:
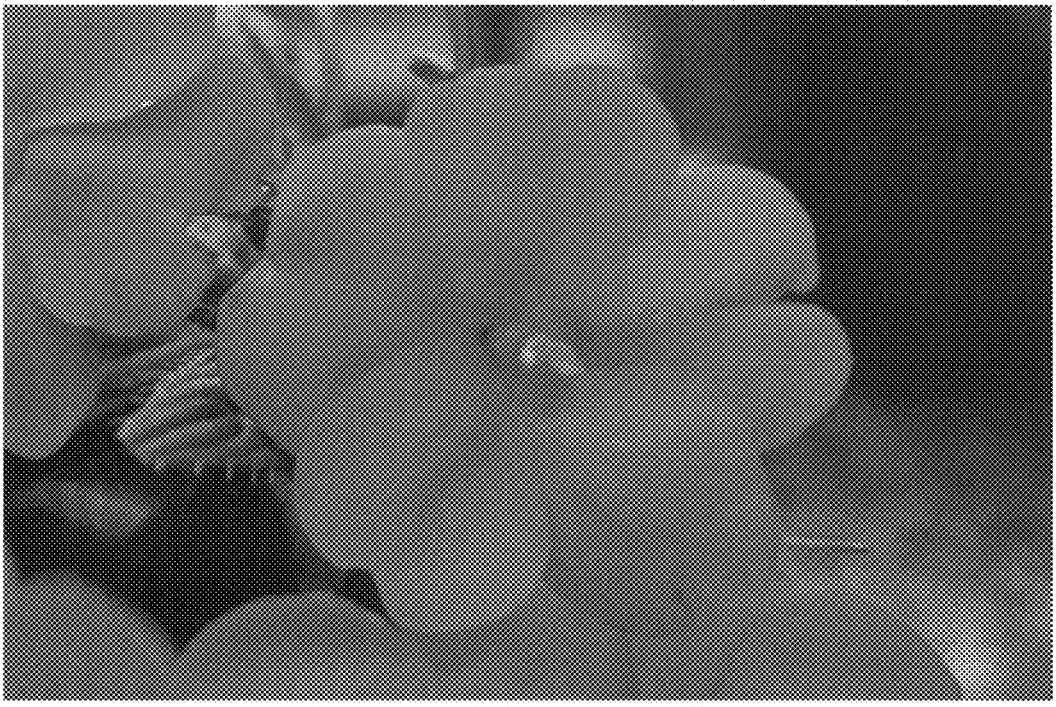
FIG. 2 shows the mature inflorescence of the plant.

The following detailed descriptions set forth the distinctive characteristics of 'SAKIMP029'. The data which define these characteristics were collected from asexual reproductions carried out in Salinas, Calif. Data was collected on plants grown one month from transplant in 8-inch pots from rooted cuttings under greenhouse conditions in Salinas, Calif. in the spring of 2013. Color references are to The R.H.S. Colour Chart of The Royal Horticultural Society of London (R.H.S.), $4^{th}$ edition (2001).

Classification:
- *Family*.—Balsaminaceae.
- *Botanical*.—*Impatiens* interspecific cross (*Impatiens hybrida hort*).
- *Common*.—*Impatiens*.
- *Designation*.—'SAKIMP029'.

Parentage:
- *Female parent*.—Proprietary *Impatiens* plant line 'NE-5331' (unpatented).
- *Male parent*.—Proprietary *Impatiens* plant line 'NH-312' (unpatented).

Growth:
- *Time to produce a rooted cutting*.—About 4 weeks.
- *Time to initiate roots*.—2 weeks.

*Rooting habit*.—Vigorous.
*Root type*.—Fibrous.
*Root color*.—RHS 155A (White).
*Environmental conditions for plant growth*.—The terminal 1.0 to 1.5 inches of an actively growing stem was excised. The vegetative cuttings were propagated in five to six weeks. The base of the cuttings were dipped for 1 to 2 seconds in a 1:9 solution of DIP 'N GROW (1 solution: 9 water) a root inducing solution immediately prior to sticking into the cell trays. Cuttings were stuck into plastic cell trays having 98 cells, and containing a moistened peat moss-based growing medium. The cuttings were misted with water from overhead for 10 seconds every 30 minutes until sufficient roots were formed. Rooted cuttings were transplanted and grown in 6-inch plastic pots in a glass greenhouse located in Salinas, Calif. Pots contained a peat moss-based growing medium. Soluble fertilizer containing 20% nitrogen, 10% phosphorus and 20% potassium was applied once a day or every other day by overhead irrigation. Pots were top-dressed with a dry, slow release fertilizer containing 20% nitrogen, 10% phosphorus and 18% potassium. The typical average air temperature was 24° C.
*Time to bloom from propagation*.—6 to 8 weeks.

Plant description:
*Habit*.—Compact.
*Life cycle*.—Annual.
*Height* (*from soil line to top of foliage*).—26.0 cm.
*Height* (*from soil to first node*).—2.0 cm.
*Spread*.—40.0 cm.
*Flowering requirements*.—Will flower so long as temperature is above 5° C.
*Temperature tolerances*.—Plants observed to continue flowering in a temperature range of 5° C. to 36° C. Plants can withstand high heat and humidity.

Branches:
*General*.—Circular cross-section, smooth.
*Number of branches*.—6 main branches Length of branches: 6.0 cm.
*Diameter of branches*.—1.0 cm.
*Length from soil to first node*.—2.0 cm.
*Internode length*.—2.0 cm.
*Color of branches*.—RHS 59A (Red-Purple).
*Anthocyanin*.—Absent.
*Pubescence*.—Absent.
*Texture*.—Smooth.

Stems:
*General*.—Circular cross-section, smooth.
*Stem length*.—13.0 cm.
*Diameter*.—0.5 cm.
*Internode length*.—5.0 cm.
*Color*.—RHS 59A (Red-Purple).
*Pubescence*.—Absent.
*Anthocyanin color*.—Absent.

Leaves:
*Arrangement*.—Whorled with up to 5 leaves per node, opposite if only two leaves at one node.
*Shape*.—Lanceolate, curled.
*Apex*.—Acuminate.
*Base*.—Attenuate.
*Margin*.—Entire.
*Venation*.—Pinnate.
*Venation color*.—Upper vein color: RHS 59A (Red-Purple). Lower vein color: RHS 59C (Red-Purple).
*Variegation*.—Absent.
*Surface appearance* (*both surfaces*).—Dull, glabrous.
*Pubescence*.—Absent.
*Length*.—11.0 cm.
*Width*.—4.5 cm.
*Color*.—Upper surface: Closest to but darker than RHS 147A (Yellow-Green). Lower surface: RHS 147B (Yellow-Green).
*Petiole*.—Length: 1.5 cm. Diameter: 0.2 cm. Color: RHS 59A (Red-Purple). Texture: Smooth, glabrous. Strength: Medium.
*Fragrance*.—Absent.

Flowers:
*Total number of flowers per node*.—2 to 3 in bloom.
*Total number of flower per plant*.—Approximately 70 in bloom.
*Inflorescence type*.—Single flower with spur.
*Lastingness of individual blooms on the plant*.—14 days.
*Fragrance*.—Absent.
*Pedicel*.—Absent.

Flower buds:
*Bud surface*.—Smooth, glabrous.
*Bud length*.—1.5 cm.
*Bud diameter*.—1.0 cm.
*Bud shape*.—Deltoid, longitudinal cross-section.
*Bud color*.—RHS 60A (Red-Purple).

Peduncle:
*Peduncle length*.—5.0 cm.
*Peduncle diameter*.—0.2 cm.
*Peduncle color*.—RHS 59B (Red-Purple).
*Peduncle texture*.—Smooth, glabrous.
*Strength*.—Medium.

Corolla:
*Shape*.—Roughly circular with 5 radial petals; rotate and stellate.
*Diameter*.—6.0 cm.
*Depth*.—1.0 cm.
*Petals*.—Shape: Obcordate. Apex: Emarginate (cleaved). Margin: Entire. Base: Attenuate. Pubescence: Glabrous. Length: 3.0 cm. Width: 4.0 cm. Color: Upper: Closest to but brighter than RHS N74A (Red-Purple). Lower: RHS N74A (Red-Purple). Eye zone: RHS 59A (Red-Purple).

Spur:
*Shape*.—Tubular; curved downward.
*Length*.—5.0 cm.
*Diameter*.—0.2 cm.
*Color*.—RHS 61A (Red-Purple).
*Texture*.—Smooth, glabrous.
*Degree of curvature*.—Medium.

Calyx:
*Arrangement*.—Composed of 2 sepals.
*Sepals*.—Shape: Lanceolate, curled. Base: Obtuse. Apex: Acute. Margin: Entire. Texture (both surfaces): Smooth, glabrous. Color: RHS 60B (Red-Purple). Length: 1.5 cm. Diameter: 0.5 cm.

Reproductive organs:
*Stamen number*.—5.
*Stamen form*.—Fused; split into 4 lobes.
*Stamen color*.—Anther color: RHS 155A (White). Filament color: RHS 61A (Red-Purple).
*Pollen color*.—RHS 155D (White).
*Pollen amount*.—Abundant.
*Ovary*.—Parietal.
*Ovary surface color*.—RHS 187A (Greyed-Purple).

*Pistil number.*—1.

*Style color*.—RHS 155A (White).

*Seed production.*—Absent.

Disease and insect resistance: No particular resistance or susceptibility observed.

COMPARISON WITH PARENTAL LINES AND KNOWN VARIETY

'SAKIMP029' is a new and unique variety of *Impatiens* owing to its magenta flower color, strong root system and a vigorous growth habit. 'SAKIMP029' is distinguished from its parents mainly by flower color as shown in Table 1 below:

TABLE 1

Comparison with Parental Lines

| Characteristic | 'SAKIMP029' | Female Parent 'NE-5331' | Male Parent 'NH-312' |
|---|---|---|---|
| Flower color | Magenta | Salmon | Red |

'SAKIMP029' is a new and unique variety of *Impatiens* owing to its magenta flower color, strong root system and a vigorous growth habit. 'SAKIMP029' is most similar to the commercial *Impatiens* 'SAKIMP026' (U.S. Plant Pat. No. 24,321); however there are differences in the flower color as described in the table below (color references are to The Royal Horticultural Society Colour Chart, 4th edition):

TABLE 2

Comparison with Similar Variety

| Characteristic | 'SAKIMP029' | 'SAKIMP026' |
|---|---|---|
| Petal color, upper surface | RHS N74A (Red-Purple) | RHS 40A (Red) |
| Petal color, lower surface | RHS N74A (Red-Purple) | RHS 50B (Red) |
| Spur color | RHS 61A (Red-Purple) | RHS 53D (Red) |

We claim:

1. A new and distinct cultivar of New Guinea *Impatiens* hybrid plant as shown and described herein.

* * * * *